United States Patent [19]

Sachse et al.

[11] Patent Number: 4,756,309
[45] Date of Patent: Jul. 12, 1988

[54] ENDOSCOPE FOR REMOVAL OF TISSUE

[76] Inventor: Hans-Ernst Sachse, Lerchenstr. 55, 8500 Nuernberg 90, Fed. Rep. of Germany; Rainer E. Sachse, 72d NE 72 Ter., Miami, Fla. 33138

[21] Appl. No.: 829,103

[22] Filed: Feb. 14, 1986

[30] Foreign Application Priority Data

Feb. 14, 1985 [DE] Fed. Rep. of Germany ....... 8505354
Feb. 25, 1985 [DE] Fed. Rep. of Germany ....... 3506590

[51] Int. Cl.⁴ ............................................. A61B 17/32
[52] U.S. Cl. ....................................... 128/305; 128/6; 604/22
[58] Field of Search .......................... 604/22; 128/6–7, 128/303 R, 305

[56] References Cited

U.S. PATENT DOCUMENTS

| | | | |
|---|---|---|---|
| 2,708,437 | 5/1955 | Hutchins | 128/7 |
| 3,835,858 | 9/1974 | Hagen | 128/305 |
| 3,847,154 | 11/1974 | Nordin | 128/305 |
| 3,937,222 | 2/1976 | Banko | 128/305 |
| 4,137,920 | 2/1979 | Bonnet | 128/7 |
| 4,167,944 | 9/1979 | Banko | 128/305 |
| 4,445,509 | 5/1984 | Auth | 128/305 |
| 4,461,305 | 7/1984 | Cibley | 128/305 |
| 4,499,899 | 2/1985 | Lyons, III | 128/6 |
| 4,539,976 | 9/1985 | Sharpe | 128/6 |

Primary Examiner—C. Fred Rosenbaum
Assistant Examiner—Gene B. Kartchner
Attorney, Agent, or Firm—Keil & Weinkauf

[57] ABSTRACT

An endoscope for resecting tissue inside body cavities, the principal feature of which is that the endoscopic tube contains a shaft carrying a grinding or milling head, which allows precise removal of scar tissue or other fairly firm tissue under endoscopic control without leaving irregular or thermally damaged wound sites.

12 Claims, 3 Drawing Sheets

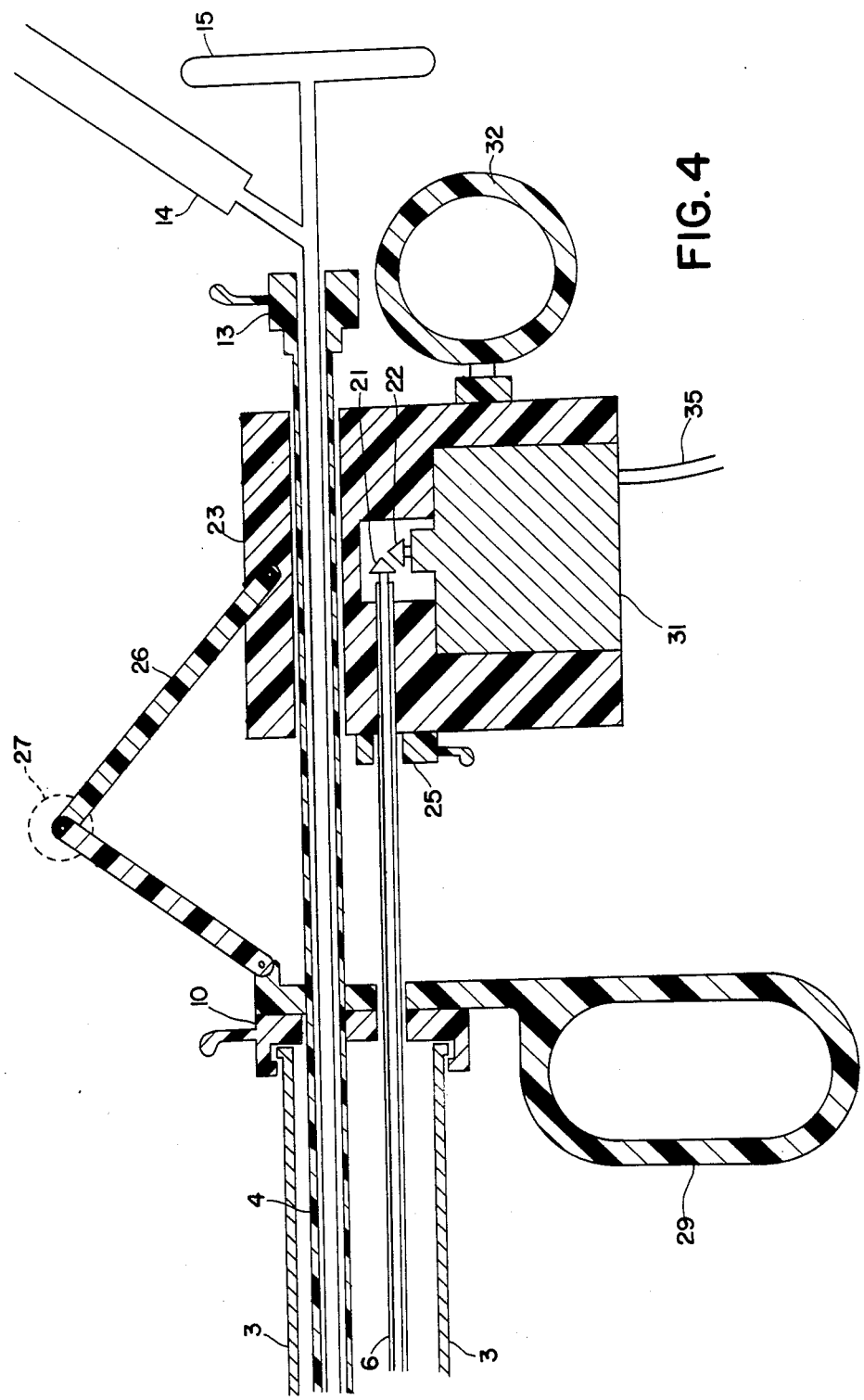

ENDOSCOPE FOR REMOVAL OF TISSUE

BACKGROUND AND SUMMARY OF THE INVENTION

This invention is directed to an improved endoscope for removing scar tissue that is constricting hollow organs of the body. It was an object of the invention to provide a means for removing tissue under visual control with high precision and in a manner that is as unstressful to the patient as possible.

The endoscopes that have been used up to now to remove tissue under visual control have involved electrical surgery, a surgical knife, or a punching device. The devices have not been entirely successful in that electrical surgery will leave a more extensive zone of dead tissue due to heat development; a surgical knife is very difficult to use due to the very small operation site and because of the limited minipulability of the cutting element, and punching or nipping devices in the form of small forceps cause uncontrolled tearing of the tissue, which leads to irregular wound areas.

The present invention allows tissue resection by means of a grinding or milling process under endoscopic observation. The grinding or milling head connected to a rotating shaft is advanced toward the tissue to be removed under visual control, and the tissue is then slowly resected under constant observation, preferably by means of the cutting surfaces of small diamonds provided on the grinding head. The present method allows millimeter-precise operation without leaving an extended zone of dead tissue, as the grinding process takes place without any significant temperature. The device further provides the continuous flushing required for good endoscopic vision which also assures continuous cooling during the grinding operation. The resulting wound areas are smooth and can be exactly adapted to the normal shape of the organ.

BRIEF DESCRIPTION OF THE DRAWINGS

The invention is shown in the drawings in which:

FIG. 4 is a longitudinal section of a further embodiment of the invention.

DETAILED DESCRIPTION

Figure 1:
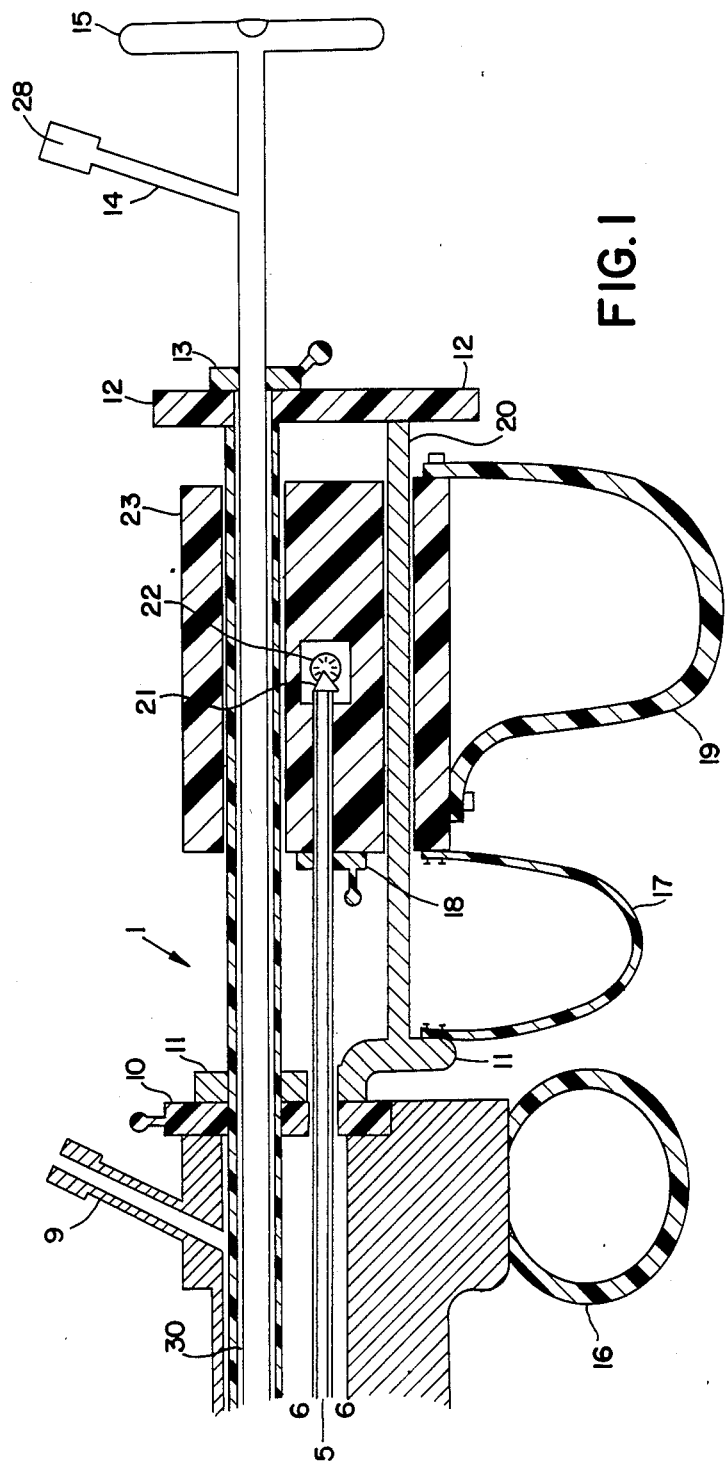
FIG. 1 is a longitudinal section through the end part of the endoscope with drive unit.
Figure 2:
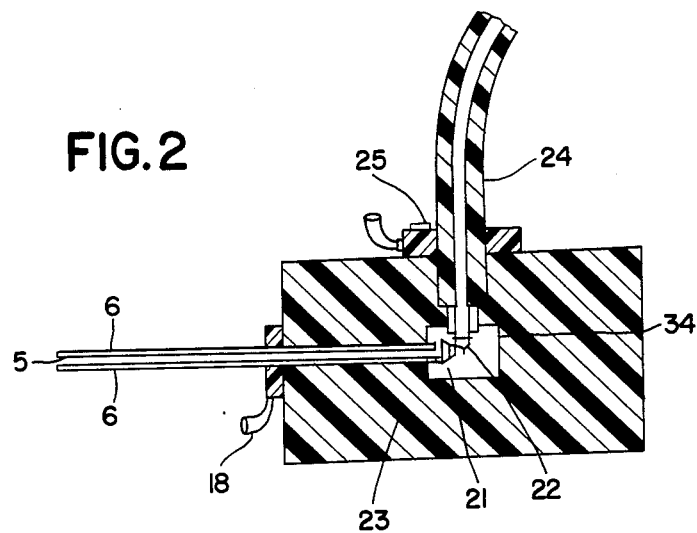
FIG. 2 is a horizontal section through the drive unit.
Figure 3:
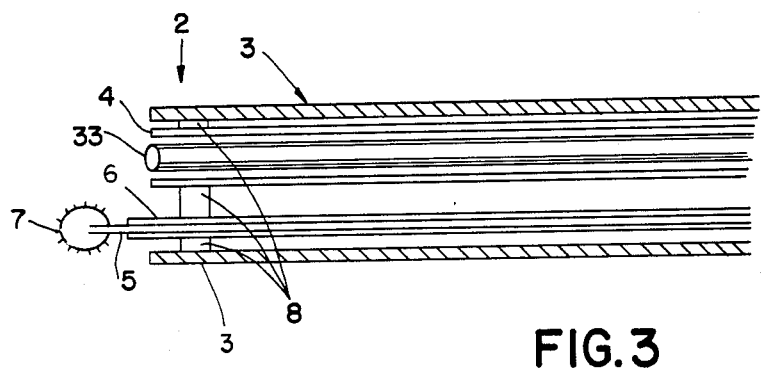
FIG. 3 is a longitudinal section through the tip of the endoscope.

The outer tube 3 of the endoscope 1 is preferably made of metal such as stainless steel or an alloy corresponding to the state of the art. As can best be seen in FIG. 3, tube 3 accommodates a tube 4 for the lens system and cold light guide and rotating shaft 5 with its bearing 6. The inlet connection 9 for flushing solutions allows the flushing solution to flow between the lens tube and the bearing of the rotating shaft through the endoscopic tube to the tip 2 of the endoscope and to flush the operation site clear.

The tubing 4 containing the lens system and the cold light guide as well as the bearing for the rotating shaft 6 is stabilized by one or more brackets 8 located within tube 3. The rotating shaft 5 carries the grinding head 7 which is provided with a screw connection for replacement purposes. A conventional locking ring 10 seals off the endoscopic tube and is connected with a sealing element 11 which is firmly fixed to the tube 4 containing the lens system with cold light guide, and which has one end of spring 17 fixed to its lower part. This spring 17 which is fastened at its other end to the drive unit, pushes the drive unit 23 away from the endoscopic tube. The drive unit can be displaced on the tube 4 containing the lens system and cold light guide as well as on a special guide rail 20 between the endoscopic tube with its locking element 11 and a limit stop plate firmly connected to the tube 4 for lens system and cold light guide against the pressure of the spring 17. These movements are controlled by the surgeon's hand holding the instrument by placing a finger into the ring 16 and gripping the handle.

When the bearing of the rotating shaft enters into the drive unit 23, the bearing will be fixed in its position by means of a conventional locking device 18 which may, for example, be in the form of a clamp attached to driving unit 23 and engaging tube 6. The conical wheel of the rotating shaft 21 meets the conical wheel of the flexible shaft 22 within chamber 34 contained within the drive unit 23. The flexible shaft 24 is fixed to the drive unit by means of a standard locking device 25. The standard locking device 13 fastens the lens system with cold light guide within its respective tube 4. Cold light is introduced through inlet 14, and the eyepiece of the lens system 15 forms the rear end of the endoscope.

Another embodiment of the invention is shown in FIG. 4. In this embodiment, the conical wheel 22 of the electric motor 31 which is supplied with electric current via a feeder cable 35. The drive unit 23 slides on tube 4 containing optical lens and cold light guide. The drive unit 23 is moved on guide rods 26 against the resistance of the spring 27. These movements are controlled by the surgeon placing his fingers into the rings 29 and 32.

List of Elements

1. Endoscope for tissue resection
2. Endoscope tip
3. Hollow outer tube of endoscope
4. Tube for lens system and cold light guide
5. Rotating shaft
6. Bearing of rotating shaft
7. Removable grinding head
8. Bracket for tube containing lens systems and cold light guide, and for rotating shaft bearing
9. Inlet connection for flushing solution
10. Locking ring for endoscopic tube
11. Locking plate firmly connected with tube containing lens system and cold light guide
12. Rear limit stop plate for movable drive unit, firmly connected with tube containing lens system and cold light guide
13. Locking system for tube containing lens system and cold light guide
14. Cold light connection
15. Eyepiece
16. Ring for surgeon's fingers
17. Spring
18. Locking system for rotating shaft bearing
19. Handle for surgeon's fingers
20. Guide rail for drive unit
21. Conical wheel of rotating shaft
22. Conical wheel of flexible shaft
23. Drive unit
24. Connection piece of flexible shaft
25. Locking system for flexible shaft on drive unit
26. Guide rods for drive unit 27. Spring for guide rods
28. Cold light cable
29. Ring for surgeon's fingers
30. Flushing duct
31. Electric motor
32. Ring for surgeon's thumb
33. Front lens of optical system
34. Chamber accommodating conical wheels
35. Electric current supply cable

We claim:

1. An endoscope which comprises: a rigid hollow tube, a lens system with a light guide extending in said tube along a longitudinal axis and having its viewing aperture in an extension of said axis, and comprising at least one flushing duct,
   wherein the hollow tube of the endoscope also contains a rigid drive shaft which is fitted with a grinding head protruding, in operation from, the tip of the endoscope, extends along an axis parallel to, but different from, the first-mentioned axis, and the other end of which is connected to a small drive unit in the endoscope for imparting continuous rotary movement to said shaft, a control element being provided to impart axial movement, independently of said rotary movement, to said drive unit and hence said shaft.

2. An endoscope according to claim 1, wherein said viewing aperture is oblique to said first-mentioned axis.

3. An endoscope according to claim 1, wherein said viewing aperture is offset and parallel to said first-mentioned axis.

4. An endoscope according to claim 1, wherein a relatively stationary control member is provided on the endoscope for cooperation with said control element in the manual actuation thereof.

5. An endoscope according to claim 1, wherein a locking device is provided which displaceably fixes said shaft to said drive unit.

6. An endoscope according to claim 1, wherein a flexible shaft is fixed to said drive unit by means of a locking device.

7. An endoscope according to claim 4, wherein said control member and said control element are in the form of a finger ring and a gripping handle, respectively.

8. An endoscope according to claim 1, wherein a spring is provided between said drive unit and said tube.

9. An endoscope according to claim 8, wherein said spring is designed to push said drive unit away from said tube.

10. An endoscope according to claim 1, wherein a bearing tube is provided for supporting said drive shaft over its full length within said hollow tube.

11. An endoscope according to claim 1, wherein said drive shaft is mounted on separate slide bearings within said hollow tube.

12. An endoscope according to claim 6, wherein a conical gear connected to said drive shaft meshes with a conical gear connected to said flexible shaft, said conical gears being disposed within a chamber contained within said drive unit.

* * * * *